United States Patent [19]
Winston et al.

[11] Patent Number: 5,958,380
[45] Date of Patent: *Sep. 28, 1999

[54] CHEWING GUM PRODUCTS AND THE USE THEREOF FOR REMINERALIZING SUBSURFACE DENTAL LESIONS AND FOR MINERALIZING EXPOSED DENTINAL TUBULES

[75] Inventors: Anthony E. Winston, East Brunswick; Norman Usen, Marlboro, both of N.J.

[73] Assignee: Enamelon, Inc., Cranbury, N.J.

[ * ] Notice: This patent is subject to a terminal disclaimer.

[21] Appl. No.: 08/888,623

[22] Filed: Jul. 7, 1997

[51] Int. Cl.⁶ .................................. A61K 9/68; A61K 7/16
[52] U.S. Cl. ............................... 424/48; 424/49; 424/57; 424/440; 426/3
[58] Field of Search ................ 424/48–58, 440; 426/3

[56] References Cited

U.S. PATENT DOCUMENTS

| | | | |
|---|---|---|---|
| 2,605,229 | 7/1952 | Marcus | 252/317 |
| 3,679,360 | 7/1972 | Rubin et al. | 23/109 |
| 3,913,229 | 10/1975 | Driskell et al. | 32/15 |
| 4,048,300 | 9/1977 | Tomlinson et al. | 424/52 |
| 4,080,440 | 3/1978 | DiGiulio et al. | 424/49 |
| 4,083,955 | 4/1978 | Grabenstetter et al. | 424/49 |
| 4,097,935 | 7/1978 | Jarcho | 3/1.9 |
| 4,108,980 | 8/1978 | Duff | 422/52 |
| 4,138,477 | 2/1979 | Gaffar | 424/52 |
| 4,150,112 | 4/1979 | Wagenknecht et al. | 424/48 |
| 4,159,315 | 6/1979 | Wagenknecht et al. | 424/48 |
| 4,177,258 | 12/1979 | Gaffar et al. | 424/52 |
| 4,183,915 | 1/1980 | Gaffar et al. | 424/52 |
| 4,233,288 | 11/1980 | Cornell | 424/48 |
| 4,265,877 | 5/1981 | Tenta | 424/48 |
| 4,348,381 | 9/1982 | Gaffar et al. | 424/52 |
| 4,397,837 | 8/1983 | Raaf et al. | 404/51 |
| 4,405,600 | 9/1983 | Besic | 424/57 |
| 4,460,565 | 7/1984 | Westrate et al. | 424/52 |
| 4,515,770 | 5/1985 | Besic | 424/49 |
| 4,518,430 | 5/1985 | Brown et al. | 106/35 |
| 4,556,561 | 12/1985 | Brown et al. | 424/151 |
| 4,565,691 | 1/1986 | Jackson | 424/52 |
| 4,606,912 | 8/1986 | Rudy et al. | 424/52 |
| 4,610,873 | 9/1986 | Rudy et al. | 424/52 |
| 4,612,053 | 9/1986 | Brown et al. | 706/35 |
| 4,672,032 | 6/1987 | Slavkin et al. | 435/68 |
| 4,824,681 | 4/1989 | Schobel et al. | 426/5 |
| 5,037,639 | 8/1991 | Tung | 424/57 |
| 5,124,160 | 6/1992 | Zibell et al. | 426/3 |
| 5,139,769 | 8/1992 | Gaffar et al. | 424/52 |
| 5,268,167 | 12/1993 | Tung | 424/52 |
| 5,378,131 | 1/1995 | Greenberg | 424/440 |
| 5,427,768 | 6/1995 | Tung | 424/52 |
| 5,437,857 | 8/1995 | Tung | 424/52 |
| 5,460,803 | 10/1995 | Tung | 424/57 |
| 5,476,647 | 12/1995 | Chow et al. | 424/52 |
| 5,571,502 | 11/1996 | Winston et al. | 424/52 |
| 5,603,922 | 2/1997 | Winston et al. | 424/49 |
| 5,605,675 | 2/1997 | Usen et al. | 424/49 |
| 5,614,175 | 3/1997 | Winston et al. | 424/52 |
| 5,645,853 | 7/1997 | Winston et al. | 424/440 |

OTHER PUBLICATIONS

J. Dent Res., vol. 76, Special Issue, p. 134, Abstract 965.
J. Dent Res., vol. 76, Special Issue, p. 255, Abstract 1931.
J. Dent Res., vol. 76, Special Issue, p. 376, Abstract 2897.

*Primary Examiner*—Shep K. Rose
*Attorney, Agent, or Firm*—Depaoli & Frenkel, P.C.

[57] ABSTRACT

This invention relates to a stable, single-part chewing gum product and methods of using same to effect remineralization of subsurface lesions in teeth and/or mineralization of exposed dentinal tubules. The chewing gum product contains a water-soluble cationic portion, a water-soluble anionic portion and a stabilizing component which substantially inhibits reaction between the cationic and anionic portions during storage of the chewing gum product but which allows the cationic and anionic portions to be simultaneously released at a substantially equal rate from the product when the product is chewed in the presence of saliva and/or water. The cationic portion is composed of at least one water-soluble calcium salt, and the anionic portion contains at least one water-soluble phosphate and, optionally, at least one water-soluble fluoride salt. The stabilizing component may be at least one water-soluble divalent metal salt other than calcium salt, the divalent metal salt being disposed in the cationic portion of the product. Alternatively, the stabilizing component may be a desiccating agent or an encapsulating coating, wherein the encapsulating coating is disposed on particles of one or both of the cationic and anionic portions.

35 Claims, No Drawings

CHEWING GUM PRODUCTS AND THE USE THEREOF FOR REMINERALIZING SUBSURFACE DENTAL LESIONS AND FOR MINERALIZING EXPOSED DENTINAL TUBULES

BACKGROUND OF THE INVENTION

This invention relates to chewing gum products and to methods of using same. More particularly, this invention relates to chewing gum products and methods of using same, wherein the chewing gum products are capable of remineralizing subsurface dental lesions and/or mineralizing exposed dentinal tubules so as to counteract caries and/or hypersensitivity, respectively.

The primary component of the enamel and dentin in teeth is calcium phosphate in the form of calcium hydroxyapatite. This material is highly insoluble at normal oral pHs. However, carious lesions can form in teeth when the teeth are subjected to acids produced from the glycolysis of sugars by the action of various oral bacteria. This is because calcium phosphate salts are more soluble in acidic media.

Saliva is supersaturated with respect to calcium and phosphate ions. Saliva, therefore, helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride-containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva, the addition of higher levels of dissolved calcium and phosphate ions is not easily accomplished.

Remineralization of dental enamel has been carried out experimentally, both in vivo and in vitro. Some studies have concentrated on the remineralizing properties of saliva and synthetic solutions supersaturated with respect to hydroxyapatite. Such studies comprise the subject matter of U.S. Pat. Nos. 3,679,360 (Rubin) and 4,097,935 (Jarcho).

Generally, the supersaturated solutions or slurries used in the Rubin and Jarcho patents for remineralization experiments have been prepared from a single form of calcium phosphate. When a carious lesion is flooded with one of these supersaturated solutions, the calcium and phosphate ions in the form of precipitated hydroxyapatite remineralize the lesion.

However, these solutions are impractical for use for several reasons. First, the amounts of calcium and phosphate ions available for remineralization in these supersaturated solutions are too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and damage the dental tissue.

U.S. Pat. Nos. 4,083,955 (Grabenstetter et al) and 4,397,837 (Raaf et al) disclose processes utilizing various dentifrices, including chewing gums, for remineralizing demineralized enamel by the consecutive treatment of tooth surfaces with separate solutions containing calcium ions and phosphate ions. Fluoride ions may be present in the phosphate solutions. It is immaterial which ionic solution is used to treat the teeth first. By sequentially applying calcium and phosphate ions to the tooth surface, high concentrations of the ions are able to diffuse or penetrate into lesions in solution form, where the ions precipitate as a calcium phosphate salt when ions from the second treatment solution diffuse in. While apparently successful, this method involves the inconvenience of employing two different chewing portions, one containing the calcium ions and the other the phosphate ions. This method could be confusing because of the necessity of ensuring the proper sequence of gum portions and also inconvenient due to the plurality of sequential applications which can be found to be time consuming.

U.S. Pat. Nos. 5,037,639 and 5,268,167 (both to Tung) disclose the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite).

According to the Tung patents, remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

International Patent WO 94/18938 (Greenberg) teaches the addition of calcium glycerophosphate to a chewing gum. The calcium glycerophosphate is said to increase calcium and phosphate concentrations in plaque, increasing remineralization and decreasing demineralization. It may also inhibit large drops in pH in plaque and interfere with metabolism of S. mutans. A problem with this technology is that the glycerophosphate ion has to hydrolyze and release free phosphate ions before it can participate in the remineralization process. Hydrolysis occurs in the mouth due to the presence of phosphatase enzymes. However, the process is slow. The high concentration of calcium ions supplied by the calcium glycerophosphate therefore has time to dissipate before sufficient phosphate can be released to produce maximum remineralization.

Thus, a problem with known remineralization compositions and techniques is that there is not a one-part, stable remineralizing composition that may be suitably prepared as a chewing gum and the like which is not negatively affected by a rise in pH or temperatures and which can efficiently remineralize teeth.

There is a need for a method of remineralizing dental enamel which uses a stable, single-part remineralizing chewing gum composition which does not require excessive amounts of calcium and phosphate salts or inordinately long, frequent or sequential exposure times.

Accordingly, a primary object of this invention is to provide a single-part, stable chewing gum product which is capable of remineralizing subsurface lesions in teeth and/or mineralizing exposed dentinal tubules in teeth.

A further object of this invention is to provide a chewing gum product having the aforementioned capabilities, wherein the chewing gum product is also easily usable by the consumer and, in terms of flavor and appearance, does not differ significantly from customary chewing gums.

These and other objects which are achieved according to the present invention can be discerned from the following description.

SUMMARY OF THE INVENTION

In the present invention, the problems of remineralization, without demineralization, are solved by applying to the teeth a stable, single-part chewing gum product which contains water-soluble cationic and anionic remineralizing portions which do not react with one another until introduced into the oral cavity. In the oral cavity, upon chewing of the chewing gum product in the presence of water and/or saliva, the cationic and anionic portions are simultaneously released from the chewing gum product at a substantially equal rate into the water and/or saliva. The release of the cationic and anionic portions into the water and/or saliva forms a mixed aqueous solution composed of cations released by the cationic portion and anions released by the anionic portion. The solution simultaneously and directly delivers the cations and anions to the tooth surface. At the tooth surface, a sufficient number of the cations and a sufficient number of the anions remain dissolved for a period of time sufficient to allow the dissolved cations and dissolved anions to diffuse through the surface of the tooth to the subsurface of the tooth. At the subsurface, the diffused cations and anions react to form an insoluble precipitate on the subsurface lesion(s) and/or exposed dentinal tubule(s) so that the lesion(s) is remineralized and/or the tubule(s) is mineralized.

Thus, it has been found that effective remineralizing treatments can be achieved by providing stable and, if desired, non-aqueous, chewing gum products, bubble gum products, dragees, and similar preparations which are comprised of soluble salts containing high concentrations of calcium, phosphate and, if desired, fluoride ions and applying them to teeth at moderate pHs. However, the calcium ions must be prevented from reacting with the phosphate ions or fluoride ions until mastication begins and then preferably prevented from rapidly precipitating so as to allow ample time for diffusion of calcium and phosphate ions into the teeth.

Accordingly, a first aspect of the present invention is directed to a stable, single-part chewing gum product capable of remineralizing subsurface lesions in teeth and/or mineralizing exposed dentinal tubules, wherein the chewing gum product contains:

(A) a water-soluble cationic portion containing an effective amount of at least one water-soluble calcium salt;

(B) a water-soluble anionic portion containing an effective amount of at least one water-soluble phosphate salt;

(C) an effective amount of a stabilizing component which is capable of substantially inhibiting reaction between the cationic and anionic portions during storage of the chewing gum product, wherein upon chewing of the chewing gum product in an oral cavity in the presence of water and/or saliva, the stabilizing component is further capable of allowing the cationic and anionic portions to be simultaneously released at a substantially equal rate from the chewing gum product into the water and/or saliva, the release of the cationic and anionic portions into the water and/or saliva yielding a mixed aqueous solution, the cationic and anionic portions each having a pH in water such that the mixed aqueous solution has a pH of from greater than about 4.0 to about 7.0; and (D) a gum base.

The chewing gum product of this invention is preferably non-aqueous.

A second aspect of this invention is directed to a dry mix composition which can be combined with a gum base to form the chewing gum product of this invention. Such dry mix composition preferably contains from about 1.0% to 80.0% of at least one water-soluble calcium salt, from about 1.0% to 80.0% of at least one water-soluble phosphate salt, from about 0.1% to 20.0% of at least one non-toxic, water-soluble divalent metal salt wherein the metal is other than calcium, and from 0 to about 1.0% of a water-soluble fluoride salt.

A third aspect of the present invention is directed to a method of remineralizing subsurface lesions and/or mineralizing exposed dentinal tubules by means of the chewing gum product of this invention. The method of this invention involves:

(1) providing the above-described chewing gum product; and (2) chewing the chewing gum product in the oral cavity in the presence of the water and/or saliva, thereby causing the product to simultaneously release at a substantially equal rate the calcium salt and the phosphate salt into the water and/or saliva, thereby forming the mixed aqueous solution having a pH of from greater than about 4.0 to about 7.0 and containing calcium cations released by the calcium salt and phosphate anions released by the phosphate salt, the mixed aqueous solution simultaneously delivering the calcium cations and phosphate anions to a surface of the at least one tooth, wherein the mixed aqueous solution has a stability such that a sufficient amount of the calcium cations and a sufficient amount of the phosphate anions remain in a dissolved state for a period of time sufficient to allow the dissolved cations and the dissolved anions to diffuse through the surface of the tooth to a subsurface thereof, wherein the dissolved, diffused cations and anions react at the subsurface to form an insoluble precipitate on the at least one subsurface lesion and/or the at least one exposed dentinal tubule, thereby effecting remineralization of the subsurface lesion and/or mineralization of the exposed dentinal tubule.

The chewing gum product of this invention is applied directly to the teeth when chewed and solubilized with saliva and/or water in the oral cavity.

The chewing gum product of this invention provides rapid remineralization of subsurface lesions.

In addition, the chewing gum product of this invention provides substantially improved subsurface remineralization and prevention of demineralization of human teeth as compared with prior art compositions. Fluoride-containing embodiments of the chewing gum of this invention are much more effective than conventional fluoride-containing dentifrices in remineralizing teeth.

Furthermore, the disadvantages of the prior art methods are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Furthermore, consumers may conveniently use the chewing gum products of this invention without substantially changing their dental care habits.

DETAILED DESCRIPTION OF THE INVENTION

The present invention provides stable, single-part chewing gum products and methods of using same to effect remineralization of subsurface dental lesions and/or mineralization of exposed dentinal tubules.

As used herein, the term "chewing gum" is meant to include not only chewing gums, but also any oral product which can be chewed, e.g., bubble gum, dragees, and the like.

As used herein, the term "single-part" with respect to the chewing gum product of this invention means that the cationic and anionic portions therein are disposed together in a single medium rather than in two separate mediums. The location of the cationic and anionic portions in a single, common medium in the chewing gum product is made possible at least in part by the use of the stabilizing component also present in the chewing gum product.

The term "stable" with respect to the chewing gum product of this invention means that the anionic and cationic portions of the chewing gum product do not substantially react with one another during storage of the product. Again, such stability is due at least in part to the use of the stabilizing component in the chewing gum product of this invention.

The present invention lies in the discovery that a distinct improvement is realized when teeth are remineralized or desensitized by the use of chewing gums containing a stabilizing component and water-soluble cationic and anionic salts, wherein the salts yield cations and anions that will react to form a desirable remineralizing or desensitizing precipitate, and the stabilizing component delays precipitation until sufficient amounts of the cations and anions have diffused to the subsurface so that precipitation occurs on the subsurface lesion(s) and/or exposed dentinal tubule(s), the precipitate being bound to the tooth structure.

As stated previously herein, the chewing gum product of this invention is composed of:

(A) a water-soluble cationic portion containing an effective amount of at least one water-soluble calcium salt;

(B) a water-soluble anionic portion containing an effective amount of at least one water-soluble phosphate salt;

(C) an effective amount of a stabilizing component which is capable of substantially inhibiting reaction between the cationic and anionic portions during storage of the chewing gum product, wherein upon chewing of the chewing gum product in an oral cavity in the presence of water and/or saliva, the stabilizing component is further capable of allowing the cationic and anionic portions to be simultaneously released at a substantially equal rate from the chewing gum product into the water and/or saliva, the release of the cationic and anionic portions into the water and/or saliva yielding a mixed aqueous solution, the cationic and anionic portions each having a pH in water such that the mixed aqueous solution has a pH of from greater than about 4.0 to about 7.0; and (D) a gum base.

As used herein with respect to the calcium salt, phosphate salt, fluoride salt and divalent metal salt, the term "water-soluble" means that at least about 0.25 gram of the salt will dissolve in 100 ml Of $H_2O$ at 200° C.

As used herein with respect to the amount of the calcium and phosphate salts, the term "effective amount" means that amount sufficient to effect substantial remineralization of subsurface lesions and/or substantial mineralization of exposed dentinal tubules.

In preferred embodiments, the chewing gum product of this invention contains from about 0.01% to about 15.0% by weight of the calcium salt and from about 0.01% to about 15.0% by weight of the phosphate salt. More preferably, the chewing gum product of this invention contains from about 0.10% to about 10.0% by weight of the calcium salt and from about 0.10% to about 10.0% by weight of the phosphate salt. In accordance with the present invention, higher levels of salts are contemplated in order to maintain calcium and phosphate concentration in the mouth for long periods. Excess salt can be present, if desired. The concentration of the water-soluble cationic salt(s) and the concentration of the water-soluble anionic salt(s) are preferably substantially equal in the present invention. Chemically equivalent concentrations of the calcium and phosphate salts are not necessary as long as the molar ratio of calcium and phosphate ions in the mixed aqueous solution is preferably from about 0.01:1 to about 100:1, more preferably from about 0.2:1 to about 5:1, and most preferably from about 1:1 to about 1.67:1.

Water-soluble calcium salts useful in the cationic portion (i.e., ingredient (A)) of the chewing gum product of this invention can be any water-soluble toxicologically harmless calcium salt. Non-limiting examples of suitable water-soluble calcium salts for use in the present invention include, for example, calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, and mixtures of the foregoing. Calcium nitrate is preferred.

Non-limiting examples of water-soluble inorganic phosphate salts which can be used in the anionic portion (i.e., ingredient (B)) of the chewing gum product of this invention include alkali-salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate.

When a chewing gum product of this invention is chewed in the oral cavity in the presence of water and/or saliva to form the mixed aqueous solution, the calcium salt in the product preferably releases to the solution at least about 100 ppm, more preferably from about 1000 ppm to about 35,000 ppm, of calcium cations, and the phosphate salt preferably releases at least about 100 ppm, more preferably from about 1000 ppm to 40,000 ppm, of phosphate anions to the solution.

If desired, water-soluble salts yielding both calcium and phosphate ions, such as monobasic-calcium orthophosphate, may be employed in the chewing gum products of this invention.

The anionic portion of the chewing gum product of this invention may also contain at least one water-soluble fluoride compound. The caries-prophylactic activity of water-soluble fluoride compounds has been established for a long time. However, because of the potential for fluorosis or other toxic effects, the concentration of fluoride ions in the mixed aqueous solution used in the present invention preferably should not exceed about 0.1% by weight. The chewing gum product may contain from about 1 ppm to 5,000 ppm of fluoride anions, but more preferably contains from about 100 ppm to about 500 ppm of fluoride anions.

Non-limiting examples of suitable water-soluble fluoride compounds for use in the present invention are the alkali fluorides such as sodium, potassium, lithium or ammonium fluoride; tin fluoride, indium fluoride, zirconium fluoride, copper fluoride, nickel fluoride, palladium fluoride, fluorozirconates such as sodium, potassium or ammonium fluorozirconate or tin fluorozirconate; fluorosilicates, fluoroborates, and fluorostannites.

Organic fluorides, such as the known amine fluorides are also suitable for use in the chewing gum product of this invention.

Water-soluble alkali metal monofluorophosphates such as sodium monofluorophosphate, lithium monofluorophosphate and potassium monofluorophosphate, preferably, sodium monofluorophosphate, are also suitable for use in the present invention. Other suitable water-soluble monofluorophosphate salts which can be used in the present invention include, e.g., ammonium monofluorophosphate, aluminum monofluorophosphate and the like.

Ingredient (C) of the chewing gum product of this invention is a stabilizing component. The stabilizing component is present in the chewing gum product of this invention in an effective amount. Such effective amount of the stabilizing component is that amount which is effective to (i) inhibit reaction between the calcium, phosphate and, if present, fluoride salts in the product during storage thereof in a closed container, and (ii) allow simultaneous release at a substantially equal rate of sufficient calcium, phosphate and, if present, fluoride ions when the product is chewed in the presence of water and/or saliva. Any orally acceptable material that stabilizes one or more of the calcium, phosphate and/or fluoride salts and prevents reaction of the salts with each other during storage of the chewing gum product in a closed container or package can be used as the stabilizing component in the chewing gum product of this invention.

In one preferred embodiment of the chewing gum product of this invention, the stabilizing component is at least one non-toxic, water-soluble divalent metal compound, wherein the divalent metal is other than calcium. The divalent metal compound is present, along with the calcium salt, in the cationic portion of the product. The presence of the divalent metal cations in the mixed aqueous solution stabilizes the system from rapidly precipitating the calcium and phosphate ions (and fluoride ions, if present). The remineralizing cations and anions can then diffuse through the tooth surface to the demineralized subsurface before forming an insoluble precipitate bound to the tooth structure. As a result, the tooth's subsurface is more effectively remineralized or desensitized when an effective amount of the divalent metal cations is utilized than when divalent metal cations are not used.

When a divalent metal salt is used as the stabilizing component in the present invention, the chewing gum product of this invention preferably contains greater than about 0.0002%, more preferably from about 0.0002% to about 1.0%, and most preferably from about 0.01% to about 1.0%, by weight of the divalent metal salt. In the mixed aqueous solution used in the present invention, the concentration of divalent metal cations is preferably at least about 10 ppm, more preferably at least about 100 ppm, with about 20,000 ppm or more being the upper limit.

As the stabilizing divalent metal compound it is, in principle, possible to employ any water-soluble, non-toxic divalent metal compound which will stabilize the calcium and phosphate ions so that they do not rapidly or prematurely precipitate before diffusing into the teeth. In practice, however, it has been found that at least one member selected from the group consisting of magnesium, strontium, tin, and zinc, with magnesium being preferred, are the most effective in stabilizing the system.

Suitable magnesium compounds are, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds are, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds are, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds are, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

In accordance with the foregoing discussion, in one preferred embodiment thereof, the chewing gum product of this invention contains: (i) preferably from about 0.05% to about 15.0%, more preferably from about 0.10% to about 10%, by weight of at least one water-soluble calcium salt; (ii) preferably more than about 0.0002%, more preferably from 0.0002% to about 1.0%, most preferably from about 0.01% to about 1.0%, by weight of at least one water-soluble divalent metal salt selected from the group consisting of magnesium, strontium, tin and zinc, with magnesium being preferred; (iii) preferably from about 0.01% to about 15.0%, more preferably about 0.10% to about 10.0%, by weight of a water-soluble phosphate salt yielding phosphate ions; (iv) optionally, from about 0.0001% to about 0.5%, preferably from about 0.0002% to about 0.01%, of a water-soluble fluoride salt; and (v) a water-insoluble gum base; wherein the pH in water of ingredients (i)–(iv) is such that a mixed aqueous solution formed when ingredients (i)–(iv) are mixed with water and/or saliva has a pH of preferably from greater than about 4.0 to about 7.0, more preferably from about 5.0 to about 5.75. Suitable pH-adjusting compounds may be used so that the pH of the mixed aqueous solution has a pH within the aforementioned ranges.

It has been found that even in the presence of divalent metal ions, some reaction between the calcium and phosphate ions may still, in fact, take place and cause some formation of insoluble calcium phosphate, etc. during storage of the chewing gum. To overcome this problem, a stabilizing component other than the divalent metal compound may be added to the chewing gum product of this invention. Such other stabilizing component, which may be used in addition to or instead of the divalent metal compound, substantially prevents reaction between the calcium ions, phosphate ions and, if present, fluoride ions.

Examples of materials other than divalent metal compounds which can be used as the stabilizing component in the chewing gum product of this invention include desiccating agents, coating or encapsulating materials and mixtures of the foregoing.

Non-limiting examples of suitable desiccating agents include magnesium sulfate, sodium sulfate, calcium sulfate, calcium chloride and colloidal silica, e.g., colloidal silica particles sintered together in chain-like formations having surface areas of from about 50 to about 400 square meters per gram, such as, for example, materials sold under the trademark Cab-O-Sil by Cabot Corp. It is believed that such materials stabilize the product of this invention by, for example, absorbing any existing water either present in or in contact with the product so as to prevent reaction of the calcium, phosphate and/or fluoride salts.

If a desiccating agent is used as the stabilizing component in the chewing gum product of this invention, the desiccating agent will preferably be present in an amount of up to about 7.5%, more preferably from about 1.0% to about 7.5%, most preferably from about 0.1% to 5%, by weight of the chewing gum product.

In accordance with the foregoing discussion, one preferred embodiment of the chewing gum product of this invention is a stable, single-part, non-aqueous chewing gum containing: (i) preferably from about 0.01% to 15.0%, more preferably about 0.10% to 10.0%, by weight of a water-soluble calcium salt; (ii) preferably from about 0.01% to 15.0%, more preferably about 0.10% to 10.0%, by weight of a water-soluble phosphate salt; (iii) optionally, from about 0.0001% to about 0.5%, preferably from about 0.0002% to 0.01%, by weight of a water-soluble fluoride salt; (iv) from about 0 to 7.5% of an orally acceptable desiccating agent; and (v) preferably from about 10.0% to 95.0% of a gum base; wherein ingredients (i)–(iii) have a pH in water such that a mixed aqueous solution formed when ingredients (i)–(iii) are mixed with water and/or saliva has a pH of preferably from greater than about 4.0 to about 7.0, more preferably from about 5.0 to about 5.75.

Another stabilizing component which can be used in the present invention to inhibit premature reaction of the calcium, phosphate and/or fluoride salts in the chewing gum product is a coating or encapsulating material disposed on the particles of one or more of the calcium, phosphate and fluoride salts. Preferred coating or encapsulating materials for use as the stabilizing component in the present invention include, e.g., oleophilic materials and, more preferably, polymeric materials. Such stabilizing coating materials prevent reaction between the active materials. In addition, the presence of the stabilizing coating on one or more of the various salts in the product of the present invention prevents reactions between the salts and other substances, for example, traces of water in or absorbed into the system.

Preferably, the stabilizing coating will be edible or rinsable from the mouth.

When used as the stabilizing component in the chewing gum product of this invention, the encapsulating coating material is preferably used in an amount of up to about 7.5%, more preferably from about 1.0% to about 7.5% and most preferably from about 0.1% to about 5%.

Non-limiting examples of encapsulating or coating materials which can function as stabilizing component (C) in the chewing gum product of this invention include oleophilic materials, conventional edible gums, polymers which exhibit proportion ranging from hydrophilic to hydrophobic (water-insoluble), resins, waxes and mineral oils.

Suitable polymer materials which can be used as the stabilizing coating in the present invention include, e.g., hydrophilic organic polymers, hydrophobic (water-insoluble) organic polymers and mixtures thereof.

Suitable hydrophilic polymers which can be used to coat the remineralizing salt particles in the chewing gum product of this invention include, e.g., water-soluble and water-dispersible organic polymers. A mixture of polymers can also be employed. A water-insoluble polymer at a concentration of from about 5.0% to 95.0 weight %, based on the coating weight, can be included with a hydrophilic polymer.

The term "hydrophilic" as employed herein with respect to organic polymers refers to an organic polymer which has a water-solubility of at least about one gram per 100 grams of water at 25° C. The term "hydrophobic" or "water-insoluble" as employed herein with respect to organic polymers refers to an organic polymer which has a water solubility of less than about one gram per 100 grams of water at 25° C.

Non-limiting examples of suitable hydrophilic polymers for coating remineralizing salt particles in the chewing gum product of this invention include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Non-limiting examples of suitable water-insoluble polymers, alone or in combination with one or more other components, for coating remineralizing salt particles in the chewing gum product of this invention include polyvinyl acetate, polyacrylamide, polyvinyl chloride, polystyrene, polyethylene, polyurethane, and the like.

The application of the polymer coating to the blend of calcium, phosphate, and other salt particles of the chewing gum product of this invention can be accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethyl formamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the discrete crystallite particles.

The coating thickness on the surface of the salt typically will vary in the range of from about 0.1 to about 20 microns. The coating can consist of a single layer or multiple layers. The polymeric coating can constitute from about 5.0% to about 50.0% of the total dry weight of the coated particles.

For purposes of releasing the core matrix of remineralizing calcium salt, phosphate salt, and, if desired, fluoride salt in the encapsulated particles when introduced into an aqueous environment, a surface coating of water-insoluble polymer may have a content of from about 5.0% to 30.0% weight percent of a particulate water-extractable organic or inorganic filler, such as sodium monosaccharide or disaccharide, sorbitol powder, mannitol, and the like.

The rate of release of remineralizing salt core matrix content of the encapsulated particles under aqueous conditions can be controlled by the quantity and type of polymer coating on the particle surface.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate.

Polyvinylpyrrolidone will release the particle core matrix content at an immediate rate, when the encapsulated particles incorporated into a chewing gum are masticated in the mouth.

The encapsulated remineralizing salt particles exhibits a unique combination of properties because of the novel physical form of the free-flowing, but substantially inert, polymer-coated particles when utilized as an ingredient in the chewing gum of this invention.

Non-limiting examples of suitable oleophilic coatings or encapsulating materials which can be used as the stabilizing component in the present invention include paraffin, mineral oil, edible oils such as peanut oil, coconut oil, palm oil, or safflower oil, oleophilic organic esters such as isopropyl silomane myristate or isopropyl palmitate, edible polysiloxanes, and the like.

Encapsulating materials containing a mixture of paraffin and waxes are also suitable.

By employing mineral oil as an oleophilic coating material for the calcium, phosphate and/or fluoride salts in the product of this invention, another advantageous characteristic is provided. Specifically, oral bacteria are known to be adversely affected by oleophilic materials. Thus, the use of a mineral oil in the product of this invention will help in removing undesired bacteria during the course of treatment.

The stabilizing coating should be of a thickness and of a composition such that the coating either readily dissolves, disperses or emulsifies in water, e.g., in the mouth during chewing, or disintegrates during such action to release the active materials, i.e., one or more of the calcium, phosphate and, if present, fluoride salts.

If the oleophilic material used for the coating is water insoluble, such as mineral oil, the coating phase can be pre-emulsified with a non-ionic, non-aqueous surfactant such as a hydrophilic ethoxylated sorbitan monooleate, e.g., the material sold under the trademark Tween. In this manner, when the composition is placed in water, the mineral oil or other oleophilic coating on the particles is emulsified more readily than without the emulsification agent being present. Other similar surfactants can be employed such as sodium lauryl sulfate and other non-ionic surfactants.

In accordance with the foregoing discussion, in one preferred embodiment thereof, the present invention provides a stable, single-part, non-aqueous chewing gum product for remineralizing subsurface lesions in teeth and/or mineralizing exposed dentinal tubules, wherein the product contains: (i) from about 0.01% to 15.0%, preferably about 0.10% to 10.0%, by weight of a water-soluble calcium salt; (ii) from about 0.01% to 15.0%, preferably about 0.10% to 10.0%, by weight of a water-soluble phosphate salt; (iii) optionally, from about 0.0001% to 0.5%, preferably from about 0.0002% to 0.01%, by weight of a water-soluble fluoride salt, (iv) an encapsulating coating disposed on at least one of the water-soluble salts, wherein the encapsulating coating either readily dissolves, disposes or emulsifies in saliva and/or water; and (v) from about 10.0% to 95.0% of a water-insoluble gum base; wherein the pH in water of ingredients (i)–(iii) is such that a mixed aqueous solution formed by combining ingredients (i)–(iii) with water and/or saliva has a pH of preferably from greater than about 4.0 to about 7.0, more preferably from about 5.0 to about 5.75.

Ingredient (D) of the chewing gum product of this invention is a water-insoluble gum base. Preferably, the chewing gum product of this invention will contain from about 5.0% to about 95.0%, more preferably from about 10.0% to about 50.0%, and most preferably from about 20% to about 35% by weight of the gum base.

The insoluble gum base used as ingredient (D) in the product of this invention is generally composed of elastomers, resins, fats and oils, softeners, and inorganic fillers. The gum base may or may not include wax. In one embodiment, the chewing gum base of the present invention preferably contains about from 20% to 60% synthetic elastomer, 0 to about 30% natural elastomer, from about 5% to 55% elastomer plasticizer, from about 4% to 35% filler, from about 5% to 35% softener, and optional minor amounts (about one percent or less) of miscellaneous ingredients such as colorants, antioxidants, etc.

Non-limiting examples of suitable synthetic elastomers include polyisobutylene with a GPC weight average molecular weight of preferably from about 10,000 to 95,000, more preferably from 50,000 to 80,000 GPC weight average molecular weight; isobutylene-isoprene copolymer (butyl elastomer); styrene-butadiene copolymers having styrene-butadiene ratios of preferably from about 1:3 up to 3:1, more preferably from 1:1 up to 1:3 bound styrene-butadiene; polyvinyl acetate having GPC weight average molecular weight of preferably from about 2,000 to about 90,000, more preferably from 10,000 to 65,000 GPC weight average molecular weight with the higher molecular weight polyvinyl acetates typically used in bubble gum base; polyisoprene; polyethylene; vinyl acetate-vinyl laurate copolymer having a vinyl laurate content of preferably from about 5% to 50%, more preferably from about 10% to 45%, by weight of the copolymer; and combinations of the foregoing.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Non-limiting examples of suitable elastomer plasticizers include natural rosin esters such as glycerol esters of partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer used.

Non-limiting examples of suitable fillers/texturizers include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g., stearic, palmitic, oleic and linoleic acids), and combinations thereof.

Colorants and whiteners may include FD&C-type dyes and lakes, fruit and vegetable extracts, titanium dioxide, and combinations thereof.

The chewing gum products of this invention may be non-aqueous. As used herein with respect to a chewing gum product of this invention, the term "non-aqueous" means that the chewing gum product does not include water in such an amount that it will adversely affect the stability required for the chewing gum product to effect remineralization and/or mineralization in accordance with the present invention, i.e., the ingredients of the chewing gum product do not contain significant quantities of free water. However, the chewing gum product may contain salts with water of hydration. Preferably, the chewing gum products of this invention contain either no water or only traces of water.

The present invention is further directed to a remineralizing/demineralizing composition in the form of a stable, one-part dry mix which can be subsequently mixed with a suitable gum base to form the chewing gum product of this invention. Such dry mix composition preferably contains from about 1.0% to 80.0% of at least one water-soluble calcium salt, from about 1.0% to 80.0% of at least one water-soluble phosphate salt, from about 0.1% to 20.0% of at least one non-toxic, water-soluble divalent metal salt wherein the metal is other than calcium, and from 0 to about 1.0% of a water-soluble fluoride salt. Suitable pH-adjusting compounds, i.e., acids, bases, or buffers, may be employed so that the pH of the mixed aqueous solution formed when the chewing gum product formed from the dry mix is chewed in the presence of water and/or saliva will preferably range from greater than about 4.0 to about 7.0, more preferably from about 5.0 to about 5.75.

The dry mix composition may further contain conventional adjuvants.

The dry mix composition may be in the form of a powder, granular material, flake or the like.

The chewing gum product formed from the dry mix composition preferably contains from about 0.005% to 20.0%, more preferably about 0.1% to 7.0%, by weight of the dry mix composition. It is preferable to provide sufficient calcium and phosphate salt in the gum to ensure that the concentrations of each exceed about 100 ppm and preferably about 1000 ppm for an extended period.

Another aspect of the present invention is directed to a method of remineralizing subsurface lesions in teeth and/or mineralizing exposed dentinal tubules by means of the chewing gum product of this invention. Such method involves the steps of:

(1) providing the chewing gum product of this invention; and (2) chewing the chewing gum product in the oral cavity in the presence of the water and/or saliva, thereby causing the product to simultaneously release at a substantially equal rate the calcium salt and the phosphate salt into the water and/or saliva, thereby forming the mixed aqueous solution having a pH of from greater than about 4.0 to about 7.0 and containing calcium cations released by the calcium salt and phosphate anions released by the phosphate salt, the mixed aqueous solution simultaneously delivering the calcium cations and phosphate anions to a surface of the at least one tooth, wherein the mixed aqueous solution has a stability such that a sufficient amount of the calcium cations and a sufficient amount of the phosphate anions remain in a dissolved state for a period of time sufficient to allow the dissolved cations and the dissolved anions to diffuse through the surface of the tooth to a subsurface thereof, wherein the dissolved, diffused cations and anions react at the subsurface to form an insoluble precipitate on the at least one subsurface lesion and/or the at least one exposed dentinal tubule, thereby effecting remineralization of the subsurface lesion and/or mineralization of the exposed dentinal tubule.

In order to effect remineralization and/or mineralization of the dental enamel, an effective amount of the desired cations and anions must be employed in the oral cavity. The amount of solution generated in the mouth preferably contains at least 100 ppm of desired cations and 100 ppm of desired anions and more preferably more than 1,000 ppm of desired cations and 1,000 ppm of desired anions. The solution preferably contains at least 10 ppm of divalent metal cations other than calcium, more preferably more than 100 ppm thereof. If a fluoride compound is employed, the chewing gum may contain from about 1 ppm to 5,000 ppm, more preferably from about 100 ppm to about 500 ppm, of fluoride anions in the oral cavity.

While the length of time of contact between the dissolved calcium and phosphate salts and the tooth's surface is not critical, it is necessary for the length of time to be great enough to allow diffusion of the ions through the tooth's surface to the demineralized subsurface. It is submitted that at least one minute of chewing is required for this diffusion and preferably it should be greater than fifteen minutes and even longer if possible. The desired extended time for such diffusion is a benefit accruing at least in part from the use of the divalent metal salts in certain embodiments of this invention.

Upon chewing of the gum product in the oral cavity with saliva and/or water, a mixed aqueous solution is formed which contains cations released by the calcium salt and, if present, the divalent metal salt, and anions released by the phosphate salt and, if present, the fluoride salt. The mixed aqueous solution has a pH of preferably from greater than about 4.0 to about 7.0, more preferably from about 5.0 to about 5.75, both before and after the precipitation reaction. The pH of the mixed aqueous solution may be adjusted to the pH desired by methods well known in the art. The pH may be controlled by the addition of any acid which is safe for use In the oral cavity and which yields the desired pH at the amount employed. Examples of suitable acids are acetic acid, phosphoric acid, hydrochloric acid, citric acid and malic acid; by the addition of a base, for example, sodium hydroxide; or buffered, for example with sodium citrate benzoate, carbonate, or bicarbonate, disodium hydrogen phosphate, sodium dihydrogen phosphate, etc. Preferably the remineralizing salts employed can be selected to obtain the desired pH. Usually a combination of monobasic, dibasic and/or tribasic alkali metal phosphate salt is selected to provide the target pH.

The mixed aqueous solution must be compatible in the oral environment. The solutions in the oral cavity and the insoluble precipitates formed therefrom must have acceptable levels of toxicity (i.e., the particular ions, in the amounts used in the remineralization process, must be non-toxic). The ions in the mixed aqueous solution must not combine prematurely in the solution to form a precipitate, but some of the ions must be able to diffuse through the surface of the tooth to a demineralized subsurface area and be able to form an insoluble salt with their counter ions.

With regard to the length of time of exposure to the teeth of the mixed aqueous solution formed in the oral cavity, it is necessary that the period of time be great enough to allow diffusion of the ions into the demineralized subsurface. At least about one minute is required for the release of the salts from the gum and for diffusion. The chewing gum is preferably masticated with the teeth for from about 5 minutes to about 15 minutes or more. The pH of the solution remains relatively constant after its introduction into the oral cavity. Calcium phosphate may precipitate at this pH, but most surprisingly, while some of the precipitation may occur immediately sufficient calcium, phosphate and fluoride ions remain in solution to diffuse into the teeth and remineralize the demineralized dental enamel. It is believed that the ability of the solutions to provide ions for remineralization is greatest upon their first introduction into the oral cavity, thereafter decreasing.

With the chewing gum product of this invention, mixing is achieved on the surface of the teeth while chewing. The essence of the present invention lies with the stable, single-part product and in the mixing and dissolution of the product components therein when the gum is chewed in the mouth, resulting in an aqueous solution which will precipitate calcium phosphate, calcium fluoride, or calcium fluoroapatite in the subsurface enamel of the teeth. Surprisingly, the solution can have a pH of from greater than about 4.0 to 7.0, more preferably about 5.0 to 5.75 to achieve this result. At a pH below about 3, demineralization occurs rapidly. A pH below 2.5 is generally undesirable from a safety standpoint.

At the subsurface of the tooth, the diffused cations and anions react together to form an insoluble precipitate which is disposed on the subsurface lesion(s) and/or on the exposed dentinal tubule(s). The insoluble precipitate is a calcium phosphate or hydroxyapatite, the natural constituent of tooth enamel, with or without incorporated fluoride ions. Although many precipitates are within the broad scope of this invention, by depositing a precipitate less soluble than the original enamel, the remineralized subsurface can be made to be more resistant to demineralization than was the original enamel. If a fluoride ion is utilized, the remineralized enamel is more resistant to demineralization than was the original enamel. Thus, the method of this invention not only remineralizes subsurface lesions and/or mineralizes exposed dentinal tubules, the method can also render the remineralized enamel more resistant to subsequent demineralization than was the original enamel.

While applicants do not wish the scope of the present invention to be limited by theory, it is believed that the calcium, phosphate, and, if present, the fluoride ions diffuse through the tooth surface to the demineralized subsurface and precipitate in the demineralized subsurface where they remineralize the tooth structure. This is surprising because sufficient calcium, phosphate, and fluoride ions remain soluble for a period of time sufficient to permit their diffusion into the demineralized subsurface of the dental enamel.

The chewing gum product of this invention may be any of a variety of different chewing gums, bubble gums, dragees, and the like, including low or high moisture, sugar or sugarless, wax-containing or wax-free, low calorie (via high base or low calorie bulking agents), and/or may contain other dental health agents.

In addition to a water-insoluble gum base portion, a typical chewing gum product includes a water-soluble portion and one or more flavoring agents. The water-soluble portion dissipates with a portion of the flavor over a period of time during chewing. The gum base portion is retained in the mouth throughout the chew.

The water-soluble portion can include bulk sweeteners, high intensity sweeteners, flavoring agents, softeners, emulsifiers, colors, acidulants, fillers, antioxidants, and other components that provide desired attributes.

The chewing gum product of this invention may be either sugarless or sugar-containing. However, in a preferred embodiment of the present invention, the chewing gum product is sugar-containing. This overcomes some of the sensory quality problems associated with sugarless gums. Furthermore, a sugar-containing chewing gum overcomes some of the other problems of sugarless gum. For example, some sugarless gums are poorly tolerated by some chewers, who manifest gastrointestinal disturbances because of the sugar alcohols used in sugarless gums. Softeners can be added to the chewing gum in order to optimize the chewability and mouth feel of the gum. Softeners may also provide additional sweetness such as with aqueous sugar or alditol solutions. The softeners, which are also known as plasticizers and plasticizing agents, preferably constitute from about 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in the chewing gum product of this invention.

Bulk sweeteners include both sugar and sugarless components. Bulk sweeteners typically constitute from about 5% to about 95% by weight of the chewing gum, more typically, from about 20% to about 80% by weight, and more commonly, from about 30% to about 60% by weight of the gum.

Sugar sweeteners generally include saccharide-containing components commonly known in the chewing gum art, including, but not limited to, sucrose, dextrose, maltose, dextrin, dried invert sugar, fructose, levulose, galactose, corn syrup solids, and the like, alone or in combination.

Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination with the above sweeteners. Preferred high intensity artificial sweeteners include, but are not limited to sucralose, aspartame, salts of acesulfame, alitame, saccharin and its salts, cyclamic acid and its salts, glycyrrhizin, dihydrochalccones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Usage level of the artificial sweetener will vary greatly and will depend on such factors as potency of the sweetener, rate of release, desired sweetness of the product, level and type of flavor used and cost considerations. Thus, the active level of artificial sweetener may vary from about 0.02% to 8.0% by weight of the gum product. When carriers used for encapsulation are included, the usage level of the encapsulated sweetener will be proportionately higher.

Combinations of sugar and/or sugarless sweeteners may also be used in the chewing gum product of this invention.

If a low-calorie chewing gum product is desired, a low-calorie bulking agent can be used. Non-limiting examples of low-calorie bulking agents include: polydextrose; raftilose; raftilin; fructooligosaccharides (NutraFlora); palatinose oligosaccharide; guar gum hydrolysate (Sun Fiber); or indigestible dextrin (Fibersol). However, other low-calorie bulking agents can also be used.

A variety of flavoring agents can be used in the chewing gum product of this invention. The flavoring agent can be used in preferred amounts of from about 0.1% to about 15.0%, more preferably from about 0.2% to about 5.0%, by weight of the chewing gum product. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

The chewing gum product of this invention may also contain a dental abrasive. Dental abrasives are particularly valuable in chewing gums due to the polishing action of the abrasives during mastication. As used herein, the term "dental abrasive" includes all manner and form of such materials which are normally used in toothpastes, chewing gums, and the like. Specifically, dicalcium diphosphate dehydrate is the preferred dental abrasive for use in the present invention. This particular material can also serve as an alkaline buffer as described previously herein.

Other dental abrasives which may be used in the present invention include, for example, calcium carbonate, sodium metaphosphate, aluminum hydroxide, magnesium carbonate, calcium sulphate, silicas including aerogels and xerogels, and tricalcium phosphate. The amount of dental abrasive used in the present invention preferably ranges from about 1.0% to about 30.0%, more preferably from about 1.5% to about 20.0%, by weight of the chewing gum product.

The chewing gum product of this invention may further contain glycerine. Glycerine softens and maintains the chewability of the chewing gum product for prolonged periods. Glycerine also adds to the sweetness of the chewing gum. Glycerine is preferably present in the chewing gum product at a concentration of from about 0.01% to about 10.0%, more preferably from about 0.2% to about 5.0%, by weight of the chewing gum product.

The chewing gum product may further contain water and/or a monohydric alcohol at a concentration value of preferably from about 2.0% to about 99.0%, more preferably from about 5.0% to about 70.0%, and most preferably from about 10.0% to about 50.0%, by weight of the chewing gum product. Mixtures of water and monohydric alcohol are particularly desirable. Such water/monohydric alcohol mixtures preferably contain a water:monohydric alcohol weight ratio of from about 20:1 to about 1:20, more preferably from about 10:1 to about 1:10.

Preferred monohydric alcohols are methanol, ethanol, and isopropanol, although other monohydric alcohols, such as those having up to 18 carbon atoms, may also be used in the present invention. The preferred monohydric alcohol is ethanol. It is to be understood, however, that if the product of this invention is to be ingested, ethanol is the only monohydric alcohol that should be used in the product.

A typical process for preparing the chewing gum product of this invention is as follows. The gum base is melted at a temperature of preferably from about 85° C. to about 90° C., cooled to a temperature of preferably about 78° C., and placed in a pre-warmed (about 60° C.) standard mixing kettle equipped with sigma blades. An emulsifier is then added. Next, a portion of sorbitol and glycerine is added and mixed for an additional 3 to 6 minutes. The mixing kettle is cooled, mannitol and the remainder of the sorbitol and glycerin are then added and mixing is continued. At this point in time, the temperature of the unflavored chewing gum is from about 39° C. to 42° C. A flavoring oil is then added and incorporated into the gum base, and mixing is continued. Finally, a sweetener material is added, and mixing is continued for an additional 1 to 10 minutes. The water-soluble remineralizing salts are added as the last ingredients. The final gum temperature is preferably from about 39° C. to 43° C. The chewing gum product is then discharged from the kettle, rolled, scored and formed into chewing gum pieces.

The following examples serve to provide further appreciation of the invention but are not meant in any way to restrict the effective scope of the invention. All percentages throughout the specification are by weight % unless otherwise indicated.

EXPERIMENTAL

Examples 1–3 and Controls A and B

Examples 1–3 (as well as Example 4) and Controls A and B describe protocol used to evaluate remineralizing products and illustrate their efficacy.

In Examples 1–3 and Control A, four two-portion compositions were prepared and tested for their remineralizing abilities. The formulations of the compositions prepared in Examples 1–3 and Control A are set forth in Table I below. Crest® toothpaste was used in Control B. In Examples 1–3 and Controls A and B, the pH of the mixed aqueous solution formed when the two portions of the product were combined was about 5.5.

TABLE I

Examples 1–3 and Control A: Formulations

| Ingredient | Concentration (% by weight) Example No. | | | |
|---|---|---|---|---|
| | 1 | 2 | 3 | A |
| Portion A | | | | |
| Calcium nitrate | 3.0 | 3.0 | 3.0 | 3.00 |
| Magnesium chloride | 0.4 | 0.8 | 0.8 | 0.00 |
| Glycerine | 24.0 | 24.0 | 24.0 | 24.00 |
| Water | 72.6 | 72.2 | 72.2 | 73.00 |
| Portion B | | | | |
| Monopotassium phosphate | 2.10 | 2.10 | 2.40 | 2.00 |
| Dipotassium phosphate | 0.60 | 0.60 | 0.20 | 0.70 |
| Sodium fluoride | 0.50 | 0.50 | 0.00 | 0.50 |
| Sodium MFP | 0.00 | 0.00 | 1.80 | 0.00 |
| Glycerine | 22.85 | 22.85 | 22.85 | 22.85 |
| Water | 73.95 | 73.95 | 72.75 | 73.95 |

In Examples 1–3 and Controls A and B, artificial lesions, about 50 u deep, were formed in bovine enamel chip surfaces by treating the chip surfaces with a demineralizing Carbopol gel for 72 hours. The surface hardness values of the demineralized chip surfaces were then measured.

In Examples 1–3 and Controls A and B, each test regimen cycle consisted of (i) a 30-minute demineralization in a standard demineralizing solution followed by (ii) a 5-minute treatment with the test products which were each diluted with human saliva at a ratio of 1-part product to two-portions human saliva, followed by (iii) a 60-minute remineralization in human saliva. Overnight, which was every fifth cycle, the specimens were each kept with a layer of saliva and stored in a cold room. The test ran for three days, for a total of 15 demineralization:treatment:remineralization cycles.

For the treatment cycle, the two portions of the remineralizing compositions used in Examples 1–3 and Control A were separately diluted 1 part product to 2 parts saliva and mixed together immediately before immersion of the enamel specimens therein.

After the specimens were treated with the remineralizing compositions prepared in Examples 1–3 and Control A, the surface hardness values of the treated specimens were measured. The increase in surface hardness values attained by treatment with the remineralizing compositions are set forth in Table II below. Table II also sets forth the increase in surface hardness values attained by treating a test specimen with Crest® toothpaste in Control B.

TABLE II

Examples 1–3 and Controls A and B: Increase in Surface Hardness Values

| Example No. | Increase in Surface Hardness |
|---|---|
| 1 | 62 |
| 2 | 49.0 |
| 3 | 21.0 |
| A | 20.0 |
| B | 16.0 |

The results set forth in Table II above show that the remineralizing compositions prepared in Examples 1 and 2, which contained sodium fluoride and magnesium chloride, significantly outperform the composition prepared in Control A and Crest® toothpaste used in Control B, neither of which contain magnesium chloride. The composition prepared in Example 3, which contained sodium monofluorophosphate (MFP) and magnesium chloride, performed equally to the Control A composition and better than Crest® toothpaste. This is surprising since sodium monofluorophosphate is generally less effective at promoting remineralization than is sodium fluoride.

Example 4 and Control C

In Example 4 and Control C, two two-portion compositions were prepared having the formulations shown in Table III below. The pH of the control composition was adjusted to 5.5.

TABLE III

Example 4 and Control C: Formulations

| Ingredient | Concentration (Weight %) Example No. | |
|---|---|---|
| | 4 | C |
| Portion (A) | | |
| Calcium nitrate | 3.0 | 0.0 |
| Magnesium chloride | 0.8 | 0.0 |
| Glycerine | 24.0 | 50.0 |
| Water | 72.2 | 50.0 |
| Portion (B) | | |
| Monopotassium phosphate | 0.6 | 0.0 |
| Dipotassium phosphate | 2.1 | 0.0 |
| Glycerine | 22.85 | 50.0 |
| Water | 74.45 | 50.0 |

In Example 4 and Control C, a treatment regimen similar to that conducted in Examples 1–3 and Control A was performed, with some exceptions.

For example, in Test I, the treatment time was 15 minutes using the formulation of Example 4. In Test I, five cycles per day were ran.

In Test II and Control Test III, the first cycle of the day was a 5-minute treatment with Crest® toothpaste. In Test II, cycles 2–5 were each a 15-minute treatment with the formulation of Example 4. In Control Test III, cycles 2–5 were each a 15-minute treatment with the formulation of Control C. The 15-minute treatment time was chosen to replicate what might happen if this formulation was released from a product where the treatment time might be extended to 15 minutes.

The three tests were also compared with a standard Crest® toothpaste treatment (Control Test IV) in which Crest® toothpaste was applied five times per day for 5 minutes.

Each test was run for three days for a total of twenty cycles.

The increase in surface hardness values obtained in Tests I and II and Control Tests III and IV are set forth in Table IV below.

TABLE IV

Tests I and II and Control Tests III and IV:
Increase in Surface Hardness

| Test No. | Increase in Surface Hardness |
| --- | --- |
| Test I | 10.0 |
| Test II | 13 |
| Control Test III | 6.0 |
| Control Test IV | 16 |

The results presented in Table IV show that treatments with the non-fluoride containing remineralizing formulation was effective in remineralizing teeth. Test I illustrates that it was slightly less effective on a one-to-one treatment basis with Crest toothpaste. However, Test II compared to Control Test III illustrates that it was more effective than Crest toothpaste on a five-to-one treatment basis than Crest toothpaste. When used with fluoride toothpaste, the remineralizing treatments had an additive remineralizing effect. This demonstrates that the likely positive effects of a non-fluoride product, i.e., a lozenge or candy containing the remineralizing ingredients if repeated several times a day, e.g., after eating.

Examples 5–7

Examples 5–7 illustrate various embodiments of the present invention. Examples 5–7 represent both sugarless (Examples 5 and 6) and sugar-containing (Example 7) chewing gum. Each of the chewing gums contained a divalent metal salt as a stabilizing component. The formulations of the chewing gums prepared in Examples 5–7 are presented in Table VI below.

TABLE V

Examples 5–7: Formulations

| | Concentration (Weight %) Example No. | | |
| --- | --- | --- | --- |
| Ingredient | 5 | 6 | 7 |
| Calcium lactate | 7.0 | 0 | 1.5 |
| Calcium acetate | 0 | 4.0 | 3.5 |
| Monopotassium phosphate | 2.8 | 3.3 | 4.0 |
| Dipotassium phosphate | 0.3 | 0.2 | 0.4 |
| Magnesium oxide | 0.2 | 0.3 | 0.3 |
| Gum base | 25.0 | 30.0 | 20.0 |
| Sugar | 0 | 0 | 58.5 |
| Glucose | 0 | 0 | 10.0 |
| Sorbitol powder | 34.6 | 54.85 | 0 |
| Mannitol powder | 15.0 | 0 | 0 |
| Maltitol powder | 10.0 | 0 | 0 |
| Flavor | 1.5 | 1.3 | 1.8 |
| Glycerine | 3.5 | 6.0 | 0 |
| Saccharin | 0.1 | 0 | 0 |
| Aspartame | 0 | 0.05 | 0 |

Examples 8–10

Examples 8–10 illustrate further embodiments of the present invention.

Example 8 illustrates an embodiment wherein the calcium salt is encapsulated with a hydrophilic polymer, and further wherein no divalent metal stabilizer is used.

Example 9 illustrates an embodiment wherein the calcium salt is encapsulated with a hydrophobic polymer, further wherein a divalent metal stabilizer is used.

Example 10 illustrates an embodiment wherein a desiccant is used in an anhydrous chewing gum product of this invention, further wherein no encapsulation and no divalent metal salts are used.

Table VI sets forth the formulations of the chewing gum products of Examples 8–10.

TABLE VI

Examples 8–10: Formulations

| | Concentration (Weight %) Example No. | | |
| --- | --- | --- | --- |
| Ingredient | 8 | 9 | 10 |
| Calcium lactate (Hydrophilic polymer encapsulated) | 7.0 | 0 | 0 |
| Calcium acetate | 0 | 0 | 5.0 |
| Calcium acetate (Hydrophobic polymer encapsulated) | 0 | 4.0 | 0 |
| Monopotassium phosphate | 2.8 | 3.3 | 4.0 |
| Dipotassium phosphate | 0.3 | 0.2 | 0.4 |
| Magnesium oxide | 0 | 0.3 | 0 |
| Anhydrous Magnesium Chloride (desiccant) | 0 | 0 | 1.0 |
| Gum base | 25.0 | 30.0 | 20.0 |
| Sugar | 0 | 0 | 57.8 |
| Glucose | 0 | 0 | 10.0 |
| Sorbitol (solution 70%) | 0 | 15.0 | 0 |
| Sorbitol powder | 34.8 | 39.85 | 0 |
| Mannitol powder | 15.0 | 0 | 0 |
| Maltitol powder | 10.0 | 0 | 0 |
| Flavor | 1.5 | 1.3 | 1.8 |
| Glycerine | 3.5 | 6.0 | 0 |
| Saccharin | 0.1 | 0 | 0 |
| Aspartame | 0 | 0.05 | 0 |

Examples 11 and 12

In Examples 11 and 12, additional studies were performed to illustrate remineralization hardness. The formulations for the compositions prepared in Examples 11 and 12 are set forth in Table VII below.

TABLE VII

Examples 11 and 12: Formulations

| | Concentration (Weight %) Example No. | |
| --- | --- | --- |
| Ingredient | 11 | 12 |
| Portion (A) | | |
| Calcium nitrate | 4.6 | 6.7 |
| Magnesium chloride | 0.8 | 0 |
| Stannous chloride | 0 | 0.04 |
| Water | 94.6 | 93.26 |
| Portion (B) | | |
| Dipotassium phosphate | 0.38 | 0.5 |
| Monopotassium phosphate | 2.32 | 3.4 |
| Water | 97.3 | 96.1 |

The regimen followed in Examples 1–4 was also followed in Examples 11 and 12. However, in Examples 11 and 12, half of each chip was covered with tape to serve as an untreated control.

The hardness results obtained in Examples 11 and 12 are set forth in Table VIII below.

TABLE VIII

Examples 11 and 12: Hardness Results

| Example No. | Hardness |
|---|---|
| 11 | 5.7 |
| 12 | 7.8 |

Three of the specimens from Example 11 and four specimens from Example 12 were sliced across the tape to expose both the treated and untreated portions of the lesion. SEM photomicrographs of each specimen were then prepared. Examination of the SEM photomicrographs clearly shows the presence of remineralization in six of the seven specimens examined as shown by a reduction in the holes and fissures in the treated sides of the specimens.

What is claimed is:

1. A stable, single-part chewing gum product capable of remineralizing at least one subsurface lesion and/or mineralizing at least one exposed dentinal tubule in at least one tooth, comprising:
    (A) a water-soluble cationic portion containing an effective amount of at least one water-soluble calcium salt;
    (B) a water-soluble anionic portion containing an effective amount of at least one water-soluble phosphate salt;
    (C) an effective amount of a stabilizing component which is capable of substantially inhibiting reaction between the cationic and anionic portions during storage of the chewing gum product, wherein upon chewing of the chewing gum product in an oral cavity in the presence of water and/or saliva, the stabilizing component is further capable of allowing the cationic and anionic portions to be simultaneously released at a substantially equal rate from the chewing gum product into the water and/or saliva, the release of the cationic and anionic portions into the water and/or saliva yielding a mixed aqueous solution, the cationic and anionic portions each having a pH in water such that the mixed aqueous solution has a pH of from greater than about 4.0 to about 7.0; and
    (D) a gum base.

2. A product according to claim 1, wherein the cationic and anionic portions each have a pH in water such that the pH of the mixed aqueous solution ranges from about 5.0 to about 5.75.

3. A product according to claim 1, wherein the product comprises from about 0.01% to about 15.0% by weight of the calcium salt and from about 0.01% to about 15.0% by weight of the phosphate salt.

4. A product according to claim 1, wherein the calcium salt is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, and mixtures of the foregoing.

5. A product according to claim 1, wherein the calcium salt is calcium nitrate.

6. A product according to claim 1, wherein the phosphate salt is selected from the group consisting of potassium orthophosphate, sodium orthophosphate, ammonium orthophosphate, monopotassium phosphate, dipotassium phosphate, tripotassium phosphate, monosodium phosphate, disodium phosphate and trisodium phosphate.

7. A product according to claim 1, wherein the phosphate salt is selected from the group consisting of monopotassium phosphate, dipotassium phosphate and tripotassium phosphate.

8. A product according to claim 1, wherein the anionic portion further comprises at least one water-soluble fluoride salt.

9. A product according to claim 8, wherein the product comprises no more than about 0.1% by weight of said fluoride salt.

10. A product according to claim 8, wherein said fluoride salt is selected from the group consisting of sodium fluoride, potassium fluoride, lithium fluoride, ammonium fluoride, tin fluoride, indium fluoride, zirconium fluoride, copper fluoride, nickel fluoride, palladium fluoride, fluorozirconates, fluorosilicates, fluoroborates, fluorostannites, amine fluorides, alkali metal monofluorophosphates, ammonium monofluorophosphates, and aluminum monofluorophosphates.

11. A product according to claim 8, wherein said fluoride salt is sodium fluoride.

12. A product according to claim 8, wherein said fluoride salt is sodium monofluorophosphate.

13. A product according to claim 1, wherein said stabilizing component is at least one non-toxic, water-soluble divalent metal compound, wherein the divalent metal is other than calcium, further wherein the divalent metal compound is disposed in the cationic portion of the product.

14. A product according to claim 13, wherein said product comprises more than about 0.0002% by weight of said divalent metal compound.

15. A product according to claim 13, wherein said divalent metal is selected from the group consisting of magnesium, strontium, tin, and zinc.

16. A product according to claim 13, wherein said divalent metal is magnesium.

17. A product according to claim 13, wherein said divalent metal compound is selected from the group consisting of magnesium chloride, magnesium acetate and magnesium oxide.

18. A product according to claim 1, wherein said stabilizing component is a desiccating agent.

19. A product according to claim 18, wherein said product comprises from about 1.0% to about 7.5% by weight of said desiccating agent.

20. A product according to claim 18, wherein said desiccating agent is selected from the group consisting of magnesium sulfate, sodium sulfate, calcium sulfate, calcium chloride and colloidal silica.

21. A product according to claim 1, wherein said product comprises from about 5.0% to about 95.0% by weight of said gum base.

22. A stable, one-part, dry mix composition which is capable of being mixed with a gum base to form the chewing gum product of claim 1, said dry-mix composition comprising:
    (a) from about 1.0% to 80.0% by weight of at least one water-soluble calcium salt;
    (b) from about 1.0% to 80.0% by weight of at least one water-soluble phosphate salt;
    (c) from about 0.1% to 20.0% by weight of at least one non-toxic, water-soluble divalent metal salt wherein the divalent metal is other than calcium;
    (d) and from 0 to about 1.0% of at least one water-soluble fluoride salt.

23. A method of remineralizing at least one subsurface lesion and/or mineralizing at least one exposed dentinal tubule in at least one tooth in an oral cavity, comprising the steps of:

(1) providing a stable, single-part chewing gum product comprising:
- (A) a water-soluble cationic portion containing an effective amount of at least one water-soluble calcium salt;
- (B) a water-soluble anionic portion containing an effective amount of at least one water-soluble phosphate salt;
- (C) an effective amount of a stabilizing component which is capable of substantially inhibiting reaction between the cationic and anionic portions during storage of the chewing gum product, wherein when the chewing gum product is chewed in an oral cavity in the presence of saliva and/or water, the stabilizing material is further capable of allowing the cationic and anionic portions to be released from the chewing gum product at a substantially equal rate such that the cationic and anionic portions are simultaneously released into the saliva and/or water to form a mixed aqueous solution therewith, the mixed aqueous solution containing anions released by the anionic portion and cations released by the cationic portion, the mixed aqueous solution simultaneously and directly delivering the anions and cations to at least one tooth surface in the oral cavity, the cationic and anionic portions each having a pH in water such that the mixed aqueous solution has a pH of from greater than about 4.0 to about 7.0; and
- (D) a gum base; and (2) chewing the chewing gum product in the oral cavity in the presence of said water and/or saliva, thereby causing the product to simultaneously release at a substantially equal rate the calcium salt and the phosphate salt into the water and/or saliva, thereby forming said mixed aqueous solution having a pH of from greater than about 4.0 to about 7.0 and containing calcium cations released by the calcium salt and phosphate anions released by the phosphate salt, the mixed aqueous solution simultaneously delivering the calcium cations and phosphate anions to a surface of said at least one tooth, wherein the mixed aqueous solution has a stability such that a sufficient amount of the calcium cations and a sufficient amount of the phosphate anions remain in a dissolved state for a period of time sufficient to allow said dissolved cations and dissolved anions to diffuse through said surface of the tooth to a subsurface of said tooth, wherein said dissolved, diffused cations and anions react at said subsurface to form an insoluble precipitate on said subsurface lesion and/or said exposed dentinal tubule, thereby effecting remineralization of said subsurface lesion and/or mineralization of said exposed dentinal tubule.

24. A method according to claim 23, wherein said chewing step (2) is carried out for a period of at least about 1 minute.

25. A method according to claim 23, wherein said chewing step (2) is carried out for a period of at least about 15 minutes.

26. A method according to claim 23, wherein the cationic and anionic portions each have a pH in water such that the pH of the mixed aqueous solution ranges from about 5.0 to about 5.75.

27. A method according to claim 23, wherein the anionic portion further comprises at least one water-soluble fluoride salt.

28. A method according to claim 23, wherein said stabilizing component is at least one non-toxic, water-soluble divalent metal compound, wherein the divalent metal is other than calcium, further wherein the divalent metal compound is disposed in the cationic portion of the product.

29. A method according to claim 28, wherein said product comprises more than about 0.0002% by weight of said divalent metal compound.

30. A method according to claim 28, wherein said divalent metal is selected from the group consisting of magnesium, strontium, tin, and zinc.

31. A method according to claim 28, wherein said divalent metal is magnesium.

32. A product according to claim 28, wherein said divalent metal compound is selected from the group consisting of magnesium chloride, magnesium acetate and magnesium oxide.

33. A method according to claim 23, wherein said stabilizing component is a desiccating agent.

34. A method according to claim 33, wherein said product comprises from about 1.0% to about 7.5% by weight of said desiccating agent.

35. A method according to claim 33, wherein said desiccating agent is selected from the group consisting of magnesium sulfate, sodium sulfate, calcium sulfate, calcium chloride and colloidal silica.

* * * * *